United States Patent [19]

Rosenbaum et al.

[11] Patent Number: 4,919,668

[45] Date of Patent: Apr. 24, 1990

[54] TEMPOROMANDIBULAR JOINT DISC IMPLANT

[76] Inventors: Robert S. Rosenbaum, 69 Grayfield Ave., West Roxbury, Mass. 02132; Noshir R. Menta, 50 Maugus Hill Rd., Wellesley, Mass. 02181

[21] Appl. No.: 229,243

[22] Filed: Aug. 8, 1988

[51] Int. Cl.$^5$ ............................. A61F 2/30; A61F 2/12
[52] U.S. Cl. ............................................ 623/18; 623/8
[58] Field of Search .................................... 623/18, 8

[56] References Cited

U.S. PATENT DOCUMENTS

| 4,446,578 | 5/1984 | Perkins et al. | 623/18 |
| 4,467,479 | 8/1984 | Brody | 623/18 |
| 4,502,161 | 3/1985 | Wall | 623/18 |
| 4,574,780 | 3/1986 | Manders | 623/8 |
| 4,648,880 | 3/1987 | Brauman | 623/8 |
| 4,769,036 | 9/1988 | Modir | 623/8 |

FOREIGN PATENT DOCUMENTS 8704917  8/1987  Fed. Rep. of Germany ........ 623/18

*Primary Examiner*—Richard J. Apley
*Assistant Examiner*—Stephanie L. Iantorno
*Attorney, Agent, or Firm*—E. Lieberstein

[57] ABSTRACT

A Temporomandibular Joint disc implant for functionally replacing an irreparable human temporomandibular disc formed of a compressible pouch-like body having at least one outer surface layer of resilient biocompatible material enclosing a filling solution or a matrix of fibrous or open-cell material(s) and a filling solution. The fluid forming the filling solution is adapted to be introduced into the body through the surface layer(s) when surgically implanting the disc.

9 Claims, 2 Drawing Sheets

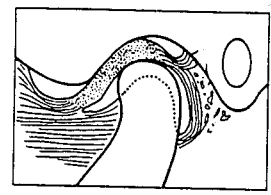
FIG. IA
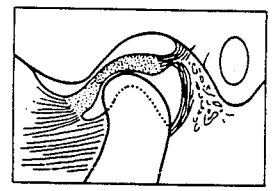
FIG. IB
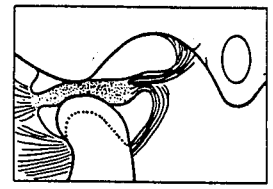
FIG. IC
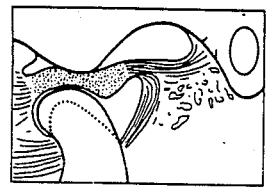
FIG. ID

TEMPOROMANDIBULAR JOINT DISC IMPLANT

BACKGROUND OF THE INVENTION

This invention relates to a prefabricated prosthetic replacement for a temporomandibular joint (TM Joint) disc in the human jaw.

In dentistry, there is a newly emerging specialty which treats Craniomandibular-Cervical Pain Dysfunction Syndrome. This syndrome is a neuromuscular and musculoskeletal dysfunction which is responsible for producing symptoms as diverse as facial pain, headaches, neckaches and locking of the jaw. Additional symptoms may be ringing in the ears, unilateral deafness, blurry vision, photophobia, nausea and dizziness. Because the syndrome produces symptoms which are so diverse, we organize them into a triad of dysfunctions in the cervical spine, the muscles of the head and neck, and the temporomandibular joint.

The Temporomandibular Joint Pain Dysfunction Syndrome occurs following pathological stretching, tearing and trauma to the ligaments and soft tissues of the TM Joint. Stretching and tearing of ligaments leads to pathological repositioning of the TM Joint disc and the symptoms that originate from the joint are pain and limitation of opening the mouth.

Since an apparent function of the disc is to provide stability within the joint, the various pathological changes that occur may result in destabilization of the joint. The disc may no longer be available to cradle the condyle and maintain contact between the condyle and the posterior slope of the eminence. To compensate for lost stability, the muscles of mastication, i.e., the masseters, temporalis, internal and external pterygoids, are thought to add stability by increasing their state of constant contraction (tonus). The additional contraction of the muscles may lead to facial pain, headaches, and neckaches of muscular origin.

Therefore, when Temporomandibular Joint Pain Dysfunction Syndrome is present, treatment may be indicated to reduce pain and dysfunction. Conventional wisdom dictates that conservative treatment in the form of bite appliances to reposition the condyle, physical therapy, and medications are the treatment of choice. However, there are patients who have undergone appropriate conservative therapy and have not been helped. For these patients, surgery may be indicated.

Attempts to treat the temporomandibular joint surgically have had limited success.

Condylectomy, or removal of the mandibular condyle, is a surgical procedure based upon the assumption that pain and dysfunction originate from the condyle. Experience with this procedure has shown that it may increase pain by changing the anatomical alignment of the mandible, causing a unilateral shift towards the side with the reduced condyle. This destabilizes the joint further and causes muscle imbalance that leads to muscle pain.

Disc plication is another surgical procedure based upon the assumption that an anteriorly displaced TM Joint disc destabilizes the joint and leads to further joint damage and muscle pain. The procedure removes the stretched posterior ligament and repositions the disc into a more physiologic position. Sutures are used to maintain the disc in the new position. When indicated, this procedure effectively treats anterior disc displacement. However, the procedure is most useful only during early stages of internal derangement when non-surgical therapy is preferable.

Since the surgeon is often called upon to treat the more advanced cases of internal derangement, removal of the TM Joint disc is sometimes needed. Some surgeons remove the TM Joint disc and do not replace it with a prosthetic implant. Non-replacement of the TM Joint disc leads to instability in the joint, the mandible, and dental malocclusion. It also subjects the TM Joint to osteoarthritic changes as a result of friction during motion.

Removal of the disc has often been followed up with implantation of a prosthetic disc to avoid complications. To date, all known prosthetic discs have yielded complications as a result of their usage. Two types of prosthetic discs have been surgically implanted composed of PROPLAST, which is a polytetrafluoroethylene-carbon composite and SILASTIC, a polydimethylsiloxane. These materials are relatively hard and the prosthetic discs formed from these materials are wired into place. Wiring is traumatic and sometimes fails to stabilize the implant. As a result the implant can migrate towards the surface and work its way out through the skin, causing infection, swelling, and pain. These implants have, in some cases, resulted in erosive osteoarthritis of the condyle, and are capable of perforating as a result of friction from the condyle.

Autologous grafts have also been tried. One type is a dermal graft donated from the skin of the thigh and used as a disc, or as a cap over the condyle, or as a cap over a repaired disc. Another type is the repositioned tendon of the temporalis muscle. Neither procedure has been clinically successful. The dermal graft may form cysts from hair follicles or may perforate. Both types subject that joint to excessive fibrous tissue formation which may cause a fibrous ankylosis.

The newest type of TM Joint surgery is arthroscopy, or microsurgery, performed through a cannula. By its nature, this procedure has limitations and as yet is unpredictable.

The conclusion in the field of TM Joint surgery at present is that removal of the disc without replacement is preferred due to lack of a suitable replacement. However, an implant of a TM Joint disc is more desirable because a disc maintains a stable joint, provides stable dental occlusion and avoids the possibility of osteoarthritic changes that can occur in a functioning joint without a disc.

SUMMARY OF THE INVENTION

The prosthetic temporomandibular joint disc of the present invention comprises a compressible pouch-like container composed of resilient biocompatible material enclosing a matrix of fibrous or open-cell material(s) and a filling solution adapted to be introduced into the container through said biocompatible material when surgically implanting said disc for forming a fluid-filled prosthesis. The matrix within the container is preferably formed from a multiplicity of fibers or an open-cell formed body and the filling solution is preferably composed of the patient's prepared plasma. A less preferred embodiment is to use a filling solution of a viscous fluid by itself without any fibers or open-cell material in the container.

BRIEF DESCRIPTION OF THE DRAWINGS

Other useful advantages of the present invention will become apparent from the following detailed description of the invention when read in conjunction with the following drawings of which:

FIGS. 1A through 1D show the progressive stages of a normal temporomandibular joint function;

DESCRIPTION OF THE PREFERRED EMBODIMENT

As a means of explaining the preferred embodiment of the present invention, it is first necessary to acquaint the reader with basic anatomy and physiology of the temporomandibular joint disc. The preferred embodiment results from simulating the shape, position, and movements of a normal disc.

Normal temporomandibular joint function is shown in FIGS. 1A through 1D. The normal TM Joint disc maintains a physiologic relationship between the mandibular condyle and the posterior slope of the eminence of the glenoid fossa. Collateral and capsular ligaments anchor the disc to the condyle and to the fossa.

In the closed-mouth position, as shown in FIG. 1A, the disc functions to maintain contact between the condyle and the posterior slope of the eminence; to maintain spatial positioning of the condyle in relationship to the eminence which then maintains stable tooth contacts; and, to stabilize the mandible (through the condyle, disc, eminence relationship). Mandibular stability is achievable by the shape of the disc, which is biconcave, i.e., the condyle rests in a thin central portion of the disc and is cradled by a thicker anterior and posterior rim.

During opening and closing of the mouth, the condyle translates, or moves, downwards and forwards along the posterior slope of the eminence. When the disc and its assembly of ligaments are healthy, the disc moves with the condyle, maintaining contact and stability between the condyle and the posterior slope of the eminence during motion. The progressive stages of normal disc function when opening the mouth is shown in FIGS. 1B through 1D, respectively.

Abnormal disc function is commonly due to macrotrauma, such as an automobile accident, or microtrauma, such as bruxism. As a result of trauma, ligaments that anchor the disc to its normal position become stretched and torn. This type of damage to the ligaments allows for abnormal repositioning of the disc into non-physiologic positions. The classical dysfunction produces an anterior displacement of the disc in a closed-mouth position. Therefore, when the patient opens the mouth, the condyle translates downward and forward, encounters the posterior rim of the displaced disc, accelerates over the posterior rim into the thin central portion of the disc, and produces a clicking sound which can be detected clinically.

Figure 2:
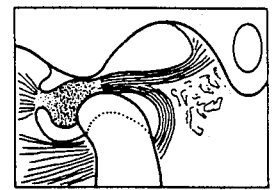
FIG. 2 shows an abnormal condition with the disc physically blocking translatory movement of the condyle.

Occasionally, when the ligaments are recently stretched and torn and the disc has repositioned itself immediately anterior to the condyle, the disc can become a physical obstruction to any movement of the condyle which creates a "closed-lock" of the mouth. This condition is evident in FIG. 2, which shows the disc immediately anterior to the condyle forming a physical obstruction to forward translation of the condyle. FIG. 2 is a single example of various pathological conditions that may result from anterior disc displacement.

Figure 3:
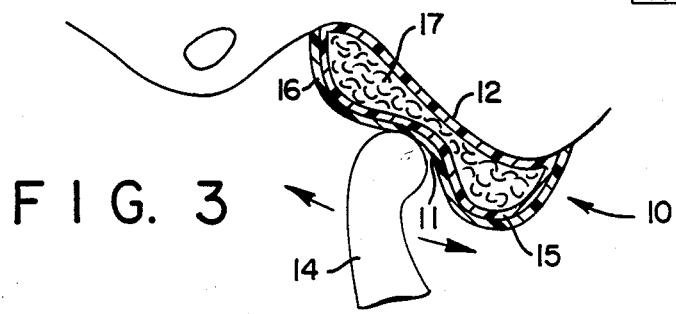
FIG. 3 is a schematic illustration in cross section of the prosthetic TM Joint disc of the present invention in the normally closed mouth position.
Figure 4:
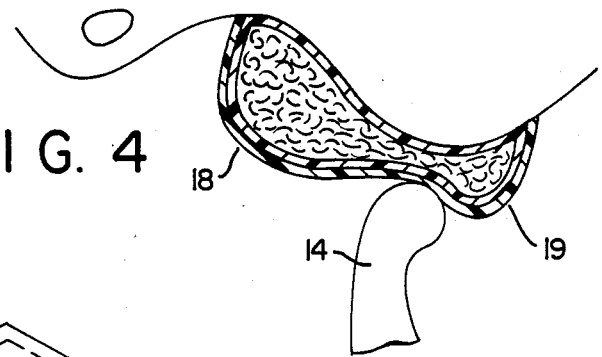
FIG. 4 shows the TM Joint disc of FIG. 3 in the normally open-mouth position.
Figure 5:
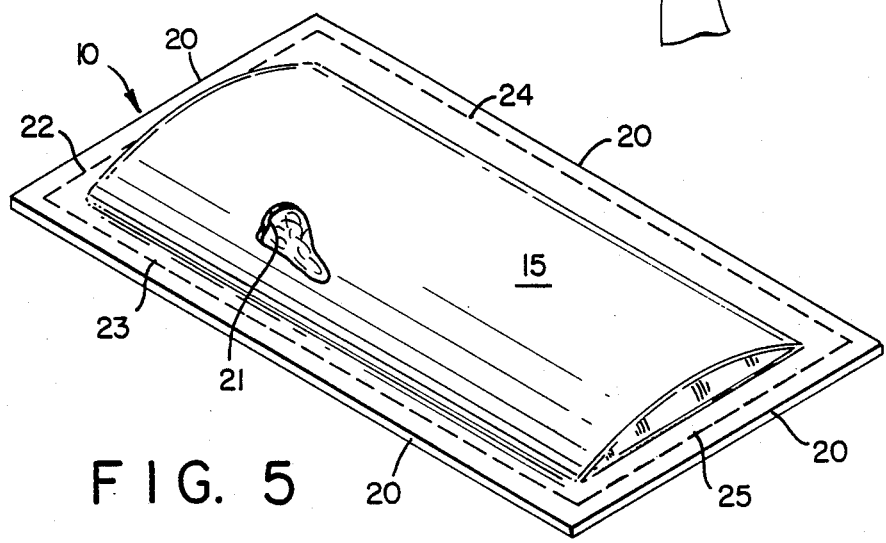
FIG. 5 is illustrative of the preferred prosthetic TM Joint disc in accordance with the present invention shown partially broken open to expose the interior matrix.

The prosthetic TM Joint disc of the present invention is illustrated in FIGS. 3, 4 and 5, respectively. When surgically implanted, the prosthesis (10) is positioned between the posterior slope of the eminence (12), i.e., the articular surface of the temporal bone and the mandibular condyle (14) and is preferably sutured in situ to the temporal bone (glenoid fossa). The TM Joint disc (10), as shown in FIG. 3, has a compressible pouch-like body (15) formed of a flexible, biocompatible material preferably of expanded polytetrafluoroethylene GORETEX enclosing a fluid-filled matrix (17), preferably of a multiplicity of fibers which may be composed of strands of expanded polytetrafluoroethylene and a liquid such as human plasma. The fluid-filled matrix (17) provides a compressible body which allows the condyle (14) to translate from a closed-mouth position, as shown in FIG. 3, to an open-mouth position, as shown in FIG. 4, by displacing fluid within the disc (10) either anteriorly or posteriorly.

The body (15) may be formed from a single membrane or layer of Goretex, or may comprise a laminate of several layers. GORETEX is the preferred material because it is available commercially as an impermeable material which is known to be substantially inert to human tissue. Moreover, the pouch-like body (15) may be sutured in place using conventional GORETEX sutures. If GORETEX is used as the body (15), an outer layer (16) of a material which resists friction, such as silicone, should be used to line the contacting surface between the condyle (14) and the body (15).

The fluid-filled matrix (17) gives the body (15) a dynamic shock absorbing characteristic for cushioning the movement of the condyle relative to the glenoid fossa thereby simulating the function of the natural TM Joint disc. Although a multiplicity of fibers saturated in fluid is preferred, an open-cell flexible cellular polymer saturated in fluid is an alternative arrangement. In addition, another alternative is the use of a filling solution of preferably plasma by itself without the fibers or open-cell polymer material. The fluid is preferably the patient's prepared plasma, although sterile saline or vitamin E oil may also be used. The fluid is preferably introduced into the body (15) when the disc is surgically implanted, as will be explained hereafter. This permits the amount of fluid added to vary, based on anatomical variations of the patient under the control of the surgeon. The pouch-like body (15) when filled with fluid should permit the body (15) to assume a normal biconcave geometry in the implanted position in contact with the condyle, so that the condyle is cradled by thicker anterior and posterior body regions (18) and (19), as shown in FIGS. 3 and 4. Important benefits are obtained by tailoring the correct amount of fluid to accurately fill the distance between the condyle and the eminence. If a disc is too thin, then condyle-disc-eminence contact is not restored and instability continues. If a disc is too thick, then it pushes the condyle and therefore the entire side of the mandible into a non-physiologic position and therefore creates a post-operative malocclusion. The size of the disc is thus under the control of the surgeon and is readily adjustable.

Temporomandibular joint function is restored by implanting the TM Joint disc (10) of the present invention in the following ways:

In the closed-mouth position, as shown in FIG. 3, the condyle (14) is seated in a thin, central portion (11) of the body (15) resulting from the displacement of fluid anteriorly and posteriorly. Simulating the characteristics of a human disc in a closed-mouth position, the prosthetic disc maintains a thinner biconcave area between the condyle and the eminence with thicker anterior and posterior rims which cradle the condyle and provide stability. Because the size of the disc is controlled by injection of fluid during the implantation procedures, the implanted disc is neither too thin to provide stability or too thick as to displace the condyle-mandible and create malocclusion.

The spatial relationship of the condyle (14) to the body (15) in the open-mouth position is shown in FIG. 4. When the condyle moves downward and forward along the posterior slope of the eminence, the normal human disc moves with the condyle maintaining the thin central portion between the condyle and the eminence for continuous stability during motion. In the present invention, the pressure of the moving condyle causes displacement of fluid so the smallest volume of fluid, corresponding to the thinnest portion of the disc is between the condyle and the eminence. Displacement of fluid causes a greater volume of fluid in front of and behind the condyle, forming thicker anterior and posterior body sections (18) and (19). Simulating the characteristics of a human disc during movements of the condyle, the prosthetic disc, although fixed in position, allows displacement of fluid by the pressure of the moving condyle which maintains the thin central region between the condyle and the eminence with thicker anterior and posterior rims which cradle the condyle, thereby maintaining joint stability at each position of the condyle during its motion.

As prolonged periods of time go by after surgical implantation of the prosthetic disc should the condyle change its spatial relationship with the glenoid fossa, as may occur from loss of vertical dimension as a result of tooth wear, tooth loss, or other occlusal conditions, the condyle may exert additional pressure against the disc. When additional pressure is exerted, if the disc were solid, it may be displaced through the bony wall of the glenoid fossa into the middle cranial fossa. In the present invention, additional pressure will only cause additional displacement of fluid laterally, instead of superiorly into the bony walls of the fossa.

The prosthetic TM Joint disc of the present invention may be implanted after symptoms of the Craniomandibular-Cervical Pain Dysfunction Syndrome are eliminated and the final vertical dimension of occlusion has been determined. If the final vertical dimension of occlusion has been determined, then the final spatial relationship between the condyle and the posterior slope of the eminence may be determined. Selection of proper disc size can be made accurately by knowing this relationship. Minor changes in condylar position that may occur in the future, such as from tooth wear, are compensated for by the flexibility of the pouch-like body (15).

If the clinician cannot eliminate the symptoms of the syndrome because the disc interferes with orthopedic repositioning of the mandible, then a two-stage procedure may be needed. The first procedure removes the disc. Phase I pain reduction through orthopedic repositioning of the mandible may then resume. The second procedure reconstructs the TM Joint by implanting the prosthetic disc and restoring joint stability.

Regardless of the surgical techniques employed, the surgeon is advised to insert a bite appliance post-operatively to unload pressure from the newly implanted disc and allow healing to occur. The bite appliance may be weaned following a healing period.

The prosthetic disc of the present invention may be manufactured in various sizes to accommodate individual anatomy.

In order to be able to readily suture the body (15) of the disc (10) to the glenoid fossa, it is preferable that the body (15) have four overhanging flaps (20), as shown in FIG. 5. The flaps (20) may readily be formed during the fabrication of the disc (10). This may be accomplished using a cylindrical open-ended tube (21) of, e.g., GORETEX as the starting material. One end of the open tube may be closed by a first row of sutures (22). Two additional rows of sutures (23) and (24) are longitudinally formed a predetermined distance from the lateral edges of the tube to form the flaps (20). The remaining open end (25) of the tube (21) is sutured closed after inserting the desired matrix (17) inside the open tube (21). During surgery the surgeon may use the flaps (20) to suture the disc (10) to the fossa. Fluid may be injected into the body (15) during the implantation procedure using, e.g., a 30-gauge needle. In this way, the surgeon can customize the final size of the disc and regulate the amount of pressure applied against the condyle. Using this method, a fibrin clot from the patient's plasma will plug the injection site. Selecting the patients own plasma may also be an advantage to avoid a foreign body reaction if plasma contacts the tissues.

What is claimed is:

1. A prosthetic temporomandibular (TM) joint disc comprising an envelope composed of a compressible biocompatible material and being sized to be positioned within the joint said envelope having a first surface adapted to engage the articular surface of the temporal bone and a second surface adapted to contact the mandibular condyle said envelope enclosing a fluid-filled medium containing a liquid-filling solution, with at least a portion of said liquid-filling solution being introduced or withdrawn from said envelope to adjust the size of said joint disc upon surgically implanting said joint disc said envelope further having at least one flap extending from said envelope composed of expanded polytetrafluoroethylene, with said flap adapted to be sutured in situ solely to soft tissue to secure said envelope within said joint.

2. A prosthetic TM Joint disc as defined in claim 1 wherein said envelope is composed of an impermeable polymer composition.

3. A prosthetic TM Joint disc as defined in claim 2 wherein said envelope is composed of an expanded polytetrafluoroethylene.

4. A prosthetic TM Joint disc as defined in claim 3 wherein said fluid-filled medium is selected from the class consisting of plasma, sterile saline, and Vitamin E.

5. A prosthetic TM Joint disc as defined in claim 4 wherein said envelope has an additional outer surface lining joined to said polytetrafluoroethylene of a composition which resists friction.

6. A prosthetic TM Joint disc as defined in claim 5 wherein said outer surface lining is formed of silicone.

7. A prosthetic TM Joint disc as defined in claim 2 wherein said envelope has four flaps extending therefrom.

8. A prosthetic TM Joint disc as defined in claim 2 wherein said fluid-filled medium comprises a matrix including a filling solution and an open-cell material selected from the class consisting of multiple fibers and a polymeric foamed body.

9. A prosthetic TM Joint disc as defined in claim 9 wherein said filling solution is selected from the class consisting of plasma, sterile saline, and Vitamin E.

* * * * *